United States Patent [19]

Gahara

[11] Patent Number: 5,195,970
[45] Date of Patent: Mar. 23, 1993

[54] COLLAPSIBLE BALLOON CATHETERS

[76] Inventor: William J. Gahara, 10 Mountain Laurels, Nashua, N.H. 03062

[21] Appl. No.: 692,015

[22] Filed: Apr. 26, 1991

[51] Int. Cl.$^5$ ............................................. A61M 29/02
[52] U.S. Cl. ........................................ 604/96; 606/194
[58] Field of Search .................... 604/96, 93, 101–103, 604/280, 282; 606/191–194

[56] References Cited

U.S. PATENT DOCUMENTS

| | | | |
|---|---|---|---|
| 2,248,934 | 7/1941 | Auzin | 18/58 |
| 4,796,629 | 1/1989 | Grayzel | 604/96 X |
| 4,941,877 | 7/1990 | Montano, Jr. | 604/96 |

FOREIGN PATENT DOCUMENTS

| | | |
|---|---|---|
| 0414350 | 2/1991 | European Pat. Off. |
| 2529083 | 12/1983 | France |
| 2187390 | 9/1987 | United Kingdom |

Primary Examiner—John D. Yasko
Attorney, Agent, or Firm—Hayes, Soloway, Hennessey & Hage

[57] ABSTRACT

A flexible plastic inflatable and collapsible medical dilatation balloon and balloon catheter wherein the internal surface of the balloon has been formed with a longitudinal geometry that prevents a flat collapsed configuration of the balloon. The internal surface of the balloon is imparted with a small raised rib configuration, which maintains a minimal contact with the internal surface of the balloon, so that the ribs remain in place along the length of the balloon. The geometry so formed on the internal surface of the balloon also increases the pressures the balloon would normally withstand when the balloon is inflated to dilate a vein or artery. The internal surface geometry can be manufactured by extrusion methods.

9 Claims, 2 Drawing Sheets

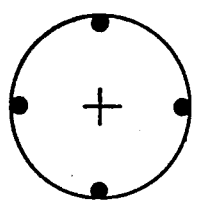
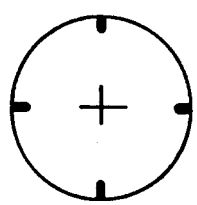
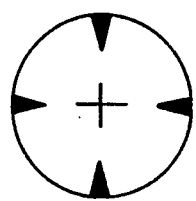
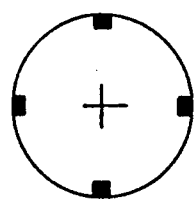
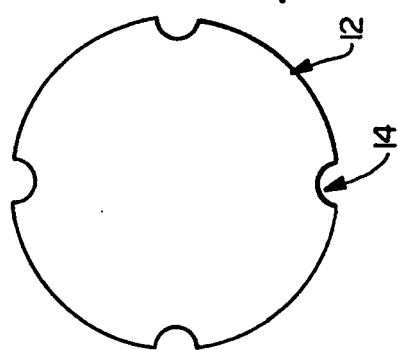
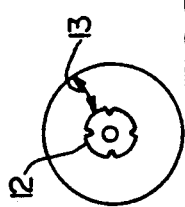
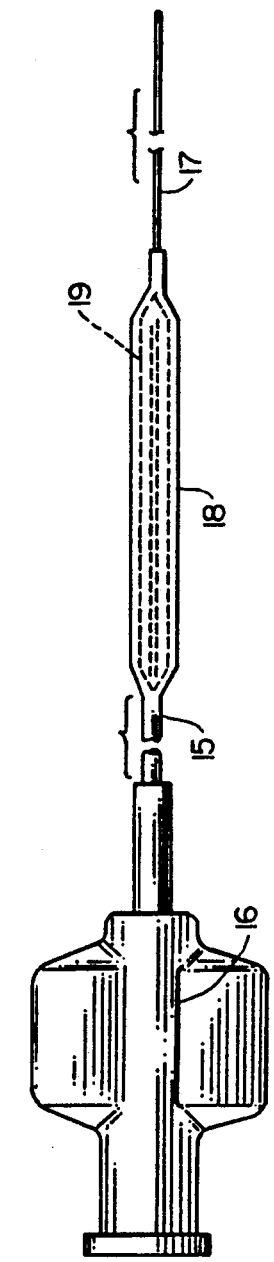

COLLAPSIBLE BALLOON CATHETERS

BACKGROUND OF THE INVENTION

1. Field of the Invention

This invention relates to balloons and to balloon catheters which are useful in medical dilatation procedures and is more particularly concerned with the development of a collapsible dilatation balloon that can withstand significant inflation pressures and upon deflation avoids the problem of "winging", that is the development of flat, lateral portions projecting laterally outward beyond the rest of the catheter.

2. Description of the Prior Art

Balloon catheters are finding increasing use in medical procedures such as percutaneous transluminal angioplasty, percutaneous transluminal nephrostomy, ureteral dilatation, biliary duct dilatation, percutaneous transluminal renal angioplasty, and the like. Balloons for use in these procedures have been prepared from a variety of polymeric materials which are blood and tissue compatible. Among those materials that have been employed include materials such as poly(vinyl-chloride), polyethylene and the like, homopolymers or copolymers of olefins, polyethylene/vinyl acetate copolymers, polyethylene terepthalate and polyurethanes.

Catheter balloons must be quite strong to withstand significant inflation pressures. Accordingly, they sometimes tend to be somewhat stiff, since their wall thickness must be sufficient to provide the necessary strength. Thus, when deflated, such catheter balloons can flatten in a phenomenon known as "winging", in which the flat, lateral portions of the deflated balloon project laterally outward beyond the rest of the catheter. This is deemed to be undesirable by many practitioners because of a concern that the flat wings may damage, e.g. an artery wall, as the deflated balloon is removed from the arterial system. Also, such flat wings can interfere with the manipulation of the catheter and its easy advancement through the arterial system.

A recent attempt to solve the problem of winging has been reported in U.S. Pat. No. 4,941,811, which describes a balloon catheter wherein the balloon defines transition zones at the respective ends which are of a rounded fluted shape. The flutes, typically from three to eight, are described as generally longitudinally directed at an angle to the balloon axis, and typically extending at a mutually perpendicular radial angle to the axis, the lateral angle being generally from 0 to about 45 degrees, preferably about 10 to 30 degrees. The radial angle in the as-molded balloon is described as dependent on the length of the transition zone and the relative diameters of the balloon and the connected catheter portions, being typically about 10 to 45 degrees. These balloons are prepared by a blow molding operation, wherein the shape of the balloon is governed by the inner shape of the molding chamber of the blow mold. Accordingly, the outer surface of the balloons, at the transition zones, contains an indentation which accounts for the grooves or flutes as defined therein. Finally, it is noted that the central portions of the catheter are directed into a mode of collapse by the flutes which is generally similar to the mode of collapse in the fluted transition zones, wherein the projecting "wings" are then avoided along the entire length of the collapsed balloon catheter.

While the above balloon apparently prevents a flat-collapsed configuration of the balloon, it does not contemplate the advantages of the instant invention, which has found that an extremely small raised ribbed configuration of essentially any geometry on the inner surface of the balloon, wherein the ribs need only maintain some minimal contact angle with the inner balloon wall, can completely prevent a flat-collapsed configuration of the balloon. Furthermore, the ribs as defined run parallel along the entire longitudinal length of the balloon and there is no need to specify a lateral or radial angle of such ribs. Such a design also provides for a much lower profile on any given catheter shaft that the balloon is employed. Moreover, the inner surface configuration described above can be manufactured by extrusion methods.

In accordance with this invention, a balloon configuration for a balloon catheter is provided, which eliminates the undesirable winging phenomena that is encountered when the catheter balloon is in a deflated condition. Also, the catheter balloon is stronger than prior art catheter balloons with improved tensile strength, while exhibiting a reduced wall thickness to improve the flexibility of the balloon. Thus, with the catheter balloon of this invention, balloon catheter procedures can be performed more effectively, with less concern about damage to the patient's veins or arteries by the "winging" phenomena of the deflated catheter balloon, and with ease of catheter advancement through the veins or artery system.

Accordingly, it is the object of this invention to overcome the "wings" using a balloon design that will collapse the balloon evenly around the catheter a full 360 degrees.

It is a further object of this invention to provide a balloon design that is suitable for use with the variety of polymeric materials that are used in dilatation balloon catherization.

Yet a further object of this invention is to provide a balloon design that will collapse the balloon evenly around the catheter a full 360 degrees while at the same time being capable of production via standard plastic melt processing techniques such as extrusion.

Still a further object of this invention is to provide a relatively small, internally ribbed, raised level, triangular, rectangular, square, circular or semi-circular parallel protrusion along the complete longitudinal internal surfaces of the dilatation balloon which can then be employed in a balloon catheter for use in a dilatation procedure such as angioplasty and the like, the internal surface modified balloon catheters being capable of withstanding higher pressures as compared to balloons without internal surface modification, which also serves to provide a lower profile balloon configuration.

These objects, and other objects which will become apparent from the description which follows, are achieved by the balloons and the balloon catheters of the invention and by the methods for their preparation. Thus, in its broadest aspect, the invention comprises balloons and balloon catheters for use in medical dilatation procedures wherein the materials employed for the preparation of the balloons can be altered during their processing and preparation into an elastic balloon configuration that collapses evenly around the surface of a dilatation catheter

SUMMARY OF THE INVENTION

The invention comprises a flexible plastic material in an inflatable and collapsible medical dilatation balloon and balloon catheter wherein the internal surface of the balloon has been integrally formed with a longitudinal geometry that prevents a flat-collapsed configuration of the balloon. The internal surface of the balloon is imparted with a small inwardly projecting raised-ribbed configuration, substantially equally spaced about the circumference of the balloon, the ribs also maintaining some minimal contact with the internal surface of the balloon so that they remain in place along the length of the balloon. The geometry so formed on the internal surface of the balloon also increases the pressure the balloon will normally withstand when the balloon is inflated to dilate a vein or artery. The internal surface geometry can be manufactured during the extrusion of a balloon tube.

BRIEF DESCRIPTION OF THE DRAWINGS

FIG. 4 shows, in cross-section, a circular geometry of the ribs on the internal surface of the collapsible balloon;

FIG. 5 shows, in cross-section, a semi-circular geometry of the ribs on the internal surface of the collapsible balloon;

FIG. 6 shows, in cross-section, a rectangular geometry of the ribs on the internal surface of the collapsible balloon;

FIG. 7 shows, in cross-section, a triangular geometry of the ribs on the internal surface of the collapsible balloon;

FIG. 8 shows, in partial cross section, a balloon and catheter in accordance with the invention;

DETAILED DESCRIPTION OF THE INVENTION

The invention will now be described by reference to the various specific embodiments which are shown in the attached drawings. It is to be understood that these embodiments are shown for purposes of illustration only and are not to be construed as limiting.

The principal novelty in the medical dilatation balloons and balloon catheters of the invention lies in their internal surface geometry which has been integrally formed with a longitudinal configuration that prevents a flat-collapsed configuration of the balloon while at the same time providing a balloon that is able to withstand higher dilatation pressures. In addition, the medical dilatation balloon catheters of the invention provide a low profile on any given catheter shaft.

The balloons and balloon catheters of the invention are prepared in a conventional manner using conventional equipment and employing any of the conventional elastomeric materials used in the fabrication of dilatation balloon catheters. Accordingly, any of the polymeric materials such as poly(vinylchloride), styrenic polymers such as "KRATON", polyacrylates, polyoelfins, polyamides, polyesters, fluoropolymers, silicones and the like, conventionally employed in the art to prepare dilatation balloon catheters, can be employed to fabricate the dilatation balloon catheters of the instant invention.

Figure 1:
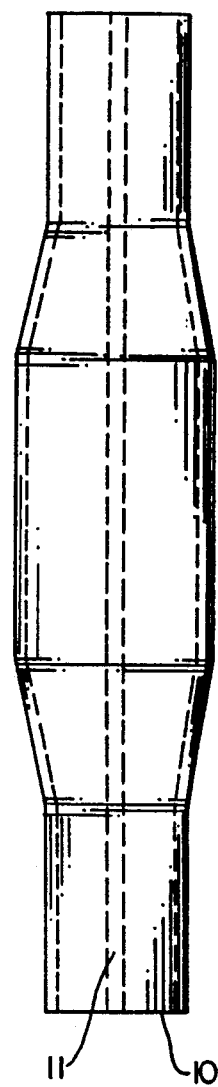
FIG. 1 shows, in cross-section, an extruded tube wherein the ribs are formed along the length of the balloon.
Figure 2:
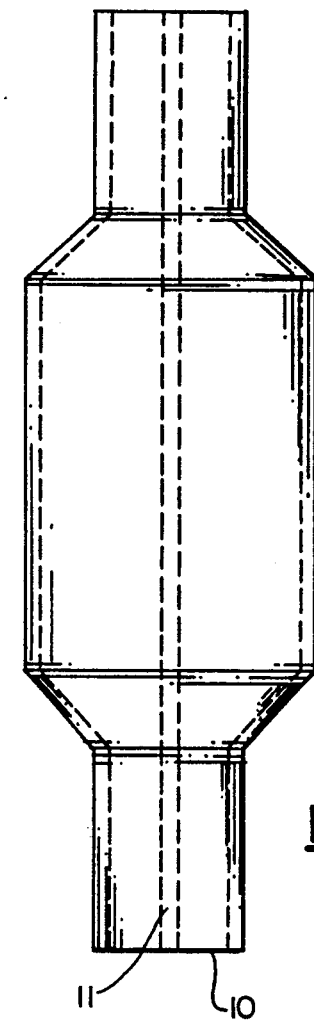
FIG. 2 shows, in cross section, another typical balloon in accordance with the invention.
Figure 3A:
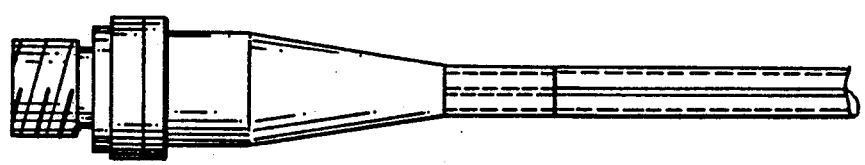
FIG. 3 shows a typical extrusion mandrel used to manufacture a typical balloon in accordance with the invention.

For example, in producing a typical dilatation balloon 10 of the kind shown overall in FIGS. 1 and 2, a tube having a wall thickness of about 0.05 mm to about 0.5 mm and an internal diameter of about 0.8 mm to about 10 mm is produced by extrusion of the aforesaid plastic materials using conventional melt processing equipment. The extruded balloon tube is formed by passing the tube over an appropriate sized mandrel which first provides the balloon with such precision wall thickness. At the same time that the mandrel operates to form the balloon tube, it can also be configured to cause the formation of the desired inner surface geometry which is shown as ribs 11 in FIGS. 1 and 2. FIG. 3 illustrates an extrusion assembly and in cross-section 12 a typical extrusion mandrel which operates to form a plurality of radially inwardly projecting ribs extending along the entire length of the extruded balloon tube. The mandrel is inserted into the extrusion die. A gap 13 is set between the die and mandrel after insertion, this gap forming the wall of the tube and also forms any design on the internal balloon wall. It can be seen that the design 14 is cut into the land area of the mandrel.

After extrusion, one end of an extruded balloon tube is inserted into a mold having an internal configuration corresponding to the external configuration of the desired balloon. The balloon tube is then pinched off at one end, the mold is heated above the softening temperature of the flexible plastic material and a suitable gas such as nitrogen is used to pressurize and inflate the softened portion of the tube and force the walls thereof into contact with the walls of the balloon.

In a more particular embodiment employing a material such as a polyurethane, the tube is heated in the mold described above to a softening temperature in the range of about 60 degrees C to about 150 degrees C.

It has been found, in accordance with the present invention, that any geometry of the internal ribs will serve to prevent a flat-collapsed configuration of the balloon. Accordingly, ribs that are triangular (FIG. 4), rectangular (FIG. 5), square, circular (FIG. 6) or semi-circular (FIG. 7), which lie parallel to one another along the complete longitudinal length on the inner surface of the balloon act to eliminate the "winging" effect encountered in balloons which lack such an internal surface modification. While the size and number of ribs can be increased for other reasons as described below, it has been found that at least three ribs are necessary to avoid the "winging" phenomena, and in a more preferred embodiment the balloons have at least four ribs.

Furthermore, the ribs may be extremely small, and in the case of a rectangular configuration, the ribs have the preferred dimensions of 0.005 inches deep by 0.003 inches wide. In the case of a round configuration, it has similarly been found that a preferred diameter of 0.0005 inches is sufficient to prevent a flat-collapsed configuration. In the broadest embodiment, it has been found that as long as the ribs protrude about 0.0001" into the balloon, "winging" can be substantially eliminated.

Furthermore, for any of the ribs now described, the ribs need only make minimum contact with the inner surface of the balloon sufficient to keep the ribs in place in a given medical dilatation procedure.

It has also been found that while the above dimensions of the ribs serve to prevent a flat-collapsed configuration of the balloon, the ribs also increase the pressures that one can apply in a dilatation procedure, again, relative to those balloons that do not contain such ribs. Accordingly, an increase in the size of the ribs will allow a further increase in the pressure that can be employed in dilatation, while still maintaining complete resistance to the development of a flat-collapsed configuration when a vacuum is applied.

The actual dimensions of the balloons with a modified internal surface geometry will depend upon the particular dilatation procedure for which the balloon and any attached catheter are to be employed. In general where the balloon is to be used in angioplasty, the external diameter of the balloon will be of the order of about 2 mm to about 25 mm. The overall length of the inflated portion will be of the order of about 10 mm to about 150 mm. The walls of the balloon will have an average thickness in the range of about 0.01 mm to about 0.2 mm depending in part on the pressures to which the balloon is to be inflated in actual use.

As will be obvious to one skilled in the art, the dilatation balloons of the invention can also be employed to replace dilatation balloons in any of the many other types of balloon-catheter combinations, with or without guide wires, currently employed in medical dilatation procedures. Referring to the drawings, FIG. 8 shows a balloon catheter, which defines a tubular catheter body 15, a proximal hub 16, and a guide wire 17 which extends through the catheter, all being of generally conventional design. Catheter body 15 defines an inflatable and collapsible balloon 18 of the invention with internal ribs 19, shown to be, as is conventional, in a tubular section of relatively larger diameter than the rest of the catheter body 15. Balloon 18 may be an integral part of the rest of the catheter body 15, or it may be separately manufactured, for example, by an extrusion process and then attached to the remainder of the catheter body 15. Balloon 18 may be entirely inflated to expand its diameter, and may also be collapsed to a minimum diameter while, by this invention, the formation of a flat "winged" configuration may be avoided in the collapsed mode of the balloon.

The balloons of the invention possess properties which render them especially valuable in carrying out medical dilatation procedures such as angioplasty and the like. Thus, the walls of the balloon are sufficiently thin to allow the balloon to deflate without a flat-collapsed configuration, and to permit passage into and through the artery, vein or like passageway involved in a medical procedure. However, the walls of the balloon are possessed of sufficient flexural strength such that the balloon will not expand beyond the originally molded configuration under pressures up to at least about 100 psi or significantly higher depending upon the wall thickness and/or overall size of the balloon. Hence, there is no problem of uncontrolled expansion or danger of bursting under pressure conditions routinely involved in angioplasty and like procedures. Further, because the balloons can be integrally molded on catheters of the same material as that used for the balloon or, alternatively, can be securely bonded without difficulty to other materials employed in the formation of catheters, there is little or no risk of rupture at the junction of balloon and catheter while the dilatation procedure is being carried out. Accordingly, the balloons and balloon catheters of the present invention represent a significant advance in the art.

The above has been offered for illustrative purposes only, and is not intended to limit the scope of the invention of this application, which is defined in the claims below.

That which is claimed is:

1. An inflatable and collapsible balloon for use in a medical dilatation catheter wherein the internal surface of the balloon has been formed with at least three radially inwardly projecting ribs which project directly into the balloon and extend along the complete longitudinal length of the inner balloon wall, the balloon and ribs being of unitary construction, wherein said construction acts to prevent a flat-collapsed configuration of the balloon.

2. The balloon of claim 1 wherein the radially inwardly projecting ribs are of a triangular, rectangular, square, circular or semi-circular geometry.

3. The balloon of claim 1 wherein the inwardly projecting ribs are substantially equally spaced about the circumference of the collapsible balloon.

4. The balloon of claim 1 wherein the inwardly projecting ribs are rectangular and are of the dimensions 0.0005 inches deep by 0.003 inches wide.

5. The balloon of claim 1 wherein the inwardly projecting ribs project 0.0001" into the balloon.

6. The balloon of claim 1 wherein the balloon is formed from a plastic material suitable for thermoplastic melt processing.

7. The balloon of claim 6 wherein the balloon is prepared from materials selected from the group consisting of poly(vinylchloride), polyethylene, ethylene copolymers, styrenic polymers, polyethylene/vinyl acetate copolymer, polyethylene terepthalate, nylon elastomers, silicone elastomers, fluoropolymer elastomers, and polyurethanes.

8. The balloon of claim 1 for use in the dilatation catheter procedure of angioplasty.

9. A catheter having a catheter body, a portion of said body defining the inflatable and collapsible balloon of claim 1.

* * * * *